United States Patent [19]

Day et al.

[11] Patent Number: 5,006,347
[45] Date of Patent: Apr. 9, 1991

[54] PROCESS FOR RETARDING BACTERIAL GROWTH IN CHEESE

[75] Inventors: Carol A. Day; Brian W. Holton, both of Worcestershire, Great Britain

[73] Assignee: Microbial Developments Ltd., England

[21] Appl. No.: 350,215

[22] Filed: May 11, 1989

Related U.S. Application Data

[62] Division of Ser. No. 189,967, May 4, 1988, Pat. No. 4,851,240.

[30] Foreign Application Priority Data

May 7, 1987 [GB] United Kingdom ............... 8710795

[51] Int. Cl.$^5$ ..................... A23C 19/00; A23C 19/097
[52] U.S. Cl. .......................................... 426/36; 426/40; 426/61; 426/582; 426/9
[58] Field of Search ..................... 426/36, 40, 61, 321, 426/334, 335, 531, 532, 18, 9, 53, 54, 635, 636, 582

[56] References Cited

U.S. PATENT DOCUMENTS 4,554,165 11/1985 Richardson ........................ 426/36

OTHER PUBLICATIONS

"Study of Possibility of Use of Bacteriophage for Cheese ...", Food Science and Technology Abstracts, No. 6, 1979, p. 1025.

"The Effect of Temperature on the Multiplication of Streptococcus ...", Australian Journal of Dairy Technology, No. 3, 1987, pp. 48–52.

*Primary Examiner*—Marianne Cintins
*Attorney, Agent, or Firm*—Ostrolenk, Faber, Gerb & Soffen

[57] ABSTRACT

The present invention discloses the use of bacteriophages for controlling unwanted fermentation of cheese by bacteria.

11 Claims, No Drawings

PROCESS FOR RETARDING BACTERIAL GROWTH IN CHEESE

This is a division of application Ser. No. 07/189,967 filed May 4, 1988, now U.S. Pat. No. 4,851,240.

FIELD OF INVENTION

The present invention relates to preparations for the prevention and treatment of microbial infestations in food-stuffs.

BACKGROUND ART

Food-stuffs are susceptible to a wide variety of microbial infestations. These are rarely beneficial and frequently harmful. Those of a harmful nature can cause mild tainting of the food-stuff, or illness ranging from mild stomach ache to death in the consumer, always assuming that the food is not rendered completely inedible.

Very few forms of infestation are likely to lead to death, but one well known example is Salmonella infection of canned products. Other harmful infestations are generally of a less serious nature but, nevertheless, spoil the product. An example of this kind is Clostridium infection, which can affect both human and animal feeds. Milk products are particularly prone to infection, especially cheese, and the result is an unpleasant acid taste combined with uncotrolled gas production, which may also cause an unsightly, deformed product.

In other areas, microbial infestation need not always be undesirable. Production of certain cheeses, for example, is totally reliant on the presence of certain fungi, and yoghurt is a thick culture of harmless bacteria.

Bacterial cultures are also of use in their own right and are becoming increasingly important with recent break-throughs in biotechnology. However, such cultures become useless if contaminated by virus (bacteriophage, or phage).

Phages were first recognised in the early 1960's. Since then, attention has been focussed on them for two reasons; their effect on the bacterial cell and their ability, in some instances, to translocate bacterial genes. This latter ability is particularly important to present day genetic studies and has enabled the development of useful gene cloning techniques. Phages are, nevertheless, being superseded by other systems less likely to damage the organisms concerned. Cultures infected by uncontrolled phage are useless, as no means are available to combat virus infection. Such cultures can only be destroyed.

DISCLOSURE OF THE INVENTION

It has now been discovered that the treatment of cheese with small amounts of phage can prevent infestation by harmful microbes.

Thus, in a first aspect of the present invention, there is provided the use of at least one species of bacteriophage in the treatment or prevention of bacterial infection in cheese or its ingredients.

In an alternative aspect of the present invention, there is provided a process for the preparation of a cheese comprising the addition of a preparation of at least one species of bacteriophage to the cheese or at least one of the ingredients therefor.

The present invention also provides preparations containing at least one variety of bacteriophage and a suitable carrier therefor for use according to either of the above described aspects of the invention.

GENERAL DESCRIPTION

Bacteriophages are highly host-specific. Extremely rapid multiplication within the host cell occurs leading to the destruction of the cell (lysis) and the release of up to 20,000 new phages, each capable of further infection. Phages are essentially non-living outside the host cell and, therefore, can exhibit very considerable longevity, making them particularly useful in preparations according to the present invention.

It will be appreciated that as bacteriophages are highly specific in the organisms they can infect, any one variety of phage will only infect one species of bacterium and, frequently, only selected strains of that species. There is thus no danger to the consumer of being infected by the phage.

A particular advantage in the use of phages according to the present invention is that, with only extremely small quantities of phage being required for efficacy, there is no adverse effect on flavour. Furthermore, as phages only infect highly specific organisms, no propagation of phage can take place in the absence of the host bacterium, so the cheese remains completely unaffected by their presence.

A disadvantage of previous antimicrobial preparations was the lack of any specificity of attack. Any antibiotic treatment resulted in the indiscriminate elimination of the natural bacterial flora, not only of the cheese, but also in the gut of the consumer. Again, phages provide the solution to this problem and can be selected against any bacterium as required.

Thus, in a further aspect of the present invention there is provided the use or process as defined above wherein the bacteriophage(s) is selected according to host bacterium specificity.

It will be appreciated that, while lysogenic phages can be used in accordance with the invention, the use of lytic phages is generally preferred, as infection results in the rapid destruction of the unwanted bacteria host.

Bacteria are known to be able to develop resistance to phage infection. The present invention, therefore, further provides a use or process as described above wherein the preparation comprises at least two strains of phage specific for one host. If the target micro-organism develops a resistance to one phage, or the phage becomes lysogenic, elimination of the unwanted organism still occurs.

Still more preferable is the 'rotation' of phages. For example, in the case where three phages are available against *clostridia* spp., then three preparations of different phage pairs are available for use in successive treatments to minimise the risk of resistance developing.

As used herein, 'rotation' means varying the bacteriophage composition of preparations according to the present invention with different batches of cheese prepared in the same locale. Such variation need not be cyclical, or even regular, provided that different compositions are used occasionally to prevent resistance developing.

Preparations according to the present invention may contain phages specific for several different species of bacterium. A suitable treatment may contain phages specific for two Clostridium and one *listeria* species, for example.

In a preferred embodiment, the present invention provides a cheese additive containing bacteriophages specific to those bacterial species most commonly found in cheese, either alone or on a carrier or base, and/or combined with other suitable additive constituents at a bacteriophage concentration of $10^2$ to $10^{12}$ pfu (plaque forming units) per ml of milk.

*Clostridia* spp. are particularly susceptible to treatment according to the present invention. Anaerobes are generally significantly less efficient than aerobes, as life processes must be restricted to essentials to allow effective exploitation of the anaerobic environment. Thus, the highly sophisticated mechanisms of the likes of *E. coli* are unavailable to anaerobes to generate a defence against phage attack.

Suitable bacteriophages for use according to the present invention may be isolated from natural sources, preferably using known bacteriophage enhancement techniques [c.f. Betz, J. V., & Anderson, K. E., (1983), J. Bact., 87, 408]. Bacteriophages so isolated may be characterised as to their host specificity by known techniques.

Suitable quantities of phage for use according to the present invention may be obtained, for example, by a batch technique, wherein a culture of host bacterium is grown nearly to capacity and then seeded with phage. After a suitable time has elapsed to allow maximal phage propagation, the culture is further lysed by chemical or physical techniques, if required, and the lysate spun down. The phage-bearing supernatant may then be further purified, for example by ultrafiltration, and concentrated (freeze-drying, for instance). The resulting preparation can be used directly or further combined with other ingredients to aid in packaging, end-use etc.

Large-scale commercial production of Clostridium-specific phages may involve initial anaerobic fermentation of the host Clostridium species, preferably in optimal submerged culture conditions for a time adequate to achieve logarithmic growth of the culture. Specific phage preparations are then introduced to the clostridial culture and incubation continued until maximal lysis can be demonstrated. Downstream recovery of such a phage preparation from solution may be effected by initial low-speed centrifugation to remove any remaining bacterial cells and debris, and the phage purified and concentrated by ultracentrifugation and ultrafiltration techniques. The resulting concentrated phage preparation can be cryoprotected and freeze-dried by techniques well-known in the art, or preferably plated onto, or mixed with, a suitable carrier material and air- or vacuum-dried as appropriate. Bacteriophages can also be encapsulated in acid-resistant biodegradable gums to provide a composite silage additive product optionally containing organic acids. Typical activity levels of phages prepared according to the above methods range from $10^9$–$10^{12}$ pfu/gram of concentrate according to the particular phage morphology.

Preparations according to the present invention suitably contain at least two varieties of phage, optionally specific for more than one family of bacterium, as required. The preparations may be liquid or solid according to requirements. Liquid preparations suitable for use in the preparation of cheese may be simple suspensions of phage in water, but preferably further comprise a suitable carrier. Suitable carriers may, for example be sugar-based, such as mannitol, but may comprise any suitable substance known in the art.

Liquid preparations may be prepared from any of the preparations generally available for similar use, a suitable quantity of phage being added. In the alternative, a more concentrated 'stock' solution may be prepared for addition to existing commercial products.

In order to determine phage activity in the final product, as well as during preparation, total specific phage counts may be undertaken using, for example, the double agar layer plating technique for plaque production, employing the host microbial species in each case. The method described by Adams, M. H., in "Bacteriophages" (Interscience Publishers (1959)) is suitable for this purpose.

In accordance with the invention, it is generally preferred for a suitable phage preparation to be added during the cheese-making process, generally at an early stage such as the rennet stage, while the mix is still liquid, to permit even dispersion throughout the cheese. This prevents small pockets of infection from occurring and spoiling the flavour, texture and appearance of the product.

The following Examples are for illustration purposes only, and are not intended to limit the scope of the present invention in any way.

EXAMPLE 1

Toxicological Trial in the Rat

A single dose oral toxicity study in the rat was performed. The procedure used met the requirements of the limit test for acute oral toxicity described in Annex V of the EEC Commission Directive relating to the classification, packaging and labelling of dangerous substances. This is an acceptable method in the assessment of additives in animal nutrition.

The test material was a mixture of equal concentration of bacteriophages specific to *Clostridium sporogenes* and to *Clostridium tyrobutyricum* at a combined level of $2 \times 10^{10}$ pfu/gram. This was administered as a single oral dose at a level of 2000 mg/kg live weight. In all cases no effects of treatment were observed and no abnormalities revealed at necropsy on termination of the study.

EXAMPLE 2

Bacteriophage Cheese Preparations

Cheeses are prepared by the normal cheese-making process with addition of clostridial phage mixtures at $10^5$–$10^7$ pfu/ml milk.

The addition of phage takes place at the rennet stage of cheese-making to avoid the heat treatment stage of the milk. This ensures phage viability. Incorporation of phage at the rennet stage also ensures even distribution of phage during formation of the curds, so that it is not entirely lost in the whey (which is usually drained off).

Thermal resistance of phage is relatively high. Most clostridial phages survive 60° C./80 mins. Heat treatment of milk for cheese-making rarely exceeds 40° C., following pasteurization so phage can be added at any stage. During and following the ripening stage, samples may be taken for phage count and Clostridium counts.

We claim:

1. A method of retarding undesirable bacterial growth in cheese comprising the administration thereto of a non-toxic amount of at least one type of bacteriophage effective to retard bacterial growth.

2. A method according to claim 1 wherein said bacteriophage is added when the cheese is being made.

3. A method according to claim 2 wherein the cheese-making includes a rennet stage and said bacteriophage is added at the rennet stage of cheese-making.

4. A method according to claim 1 wherein bacteriophage specificity is for bacteria selected from the group consisting of *Clostridia* spp. and *Listeria* spp.

5. A method according to claim 1 wherein, when said cheese is regularly prepared in the same locale, different varieties of bacteriophage are administered to different batches of cheese.

6. A method according to claim 1 wherein a bacteriophage-containing liquid is administered to said cheese so as to provide $10^2$ to $10^{12}$ pfu/ml.

7. A method according to claim 6 wherein the liquid provides $10^5$ to $10^7$ pfu/ml.

8. A method according to claim 2 wherein a bacteriophage-containing liquid is administered to said cheese so as to provide $10^2$ to $10^{12}$ pfu/ml.

9. A method according to claim 8 wherein the liquid provides $10^5$ to $10^7$ pfu/ml.

10. A method according to claim 3 wherein a bacteriophage-containing liquid is administered to said cheese so as to provide $10^2$ to $10^{12}$ pfu/ml.

11. A method according to claim 10 wherein the liquid provides $10^5$ to $10^7$ pfu/ml.

* * * * *